United States Patent [19]

Miura et al.

[11] Patent Number: 5,581,348

[45] Date of Patent: Dec. 3, 1996

[54] SURFACE INSPECTING DEVICE USING BISECTED MULTI-MODE LASER BEAM AND SYSTEM HAVING THE SAME

[75] Inventors: Seiya Miura; Michio Kohno; Takehiko Iwanaga, all of Utsunomiya, Japan

[73] Assignee: Canon Kabushiki Kaisha, Tokyo, Japan

[21] Appl. No.: 591,916

[22] Filed: Jan. 25, 1996

Related U.S. Application Data

[63] Continuation of Ser. No. 281,607, Jul. 28, 1994, abandoned.

[30] Foreign Application Priority Data

| Jul. 29, 1993 | [JP] | Japan | 5-188403 |
| Jul. 29, 1993 | [JP] | Japan | 5-188436 |

[51] Int. Cl.⁶ .................... G01N 21/00; G02B 27/10
[52] U.S. Cl. ........................... 356/237; 359/618
[58] Field of Search ............... 356/237; 250/562, 250/572; 359/629, 636–638, 618

[56] References Cited

U.S. PATENT DOCUMENTS

| 5,017,798 | 5/1991 | Murakami et al. | 250/572 |
| 5,048,926 | 9/1991 | Tanimoto | 359/618 |
| 5,105,092 | 4/1992 | Natsubori et al. | 356/237 |
| 5,162,867 | 11/1992 | Kohno | 356/237 |
| 5,359,407 | 10/1994 | Suzuki et al. | 250/572 |
| 5,381,225 | 1/1995 | Kohno | 250/572 |

FOREIGN PATENT DOCUMENTS

| 04152545 | 5/1992 | Japan | 356/237 |
| 04188746 | 7/1992 | Japan | 356/237 |

*Primary Examiner*—Frank Gonzalez
*Assistant Examiner*—Jason D. Eisenberg
*Attorney, Agent, or Firm*—Fitzpatrick, Cella, Harper & Scinto

[57] ABSTRACT

A surface state inspecting device includes an illumination system for illuminating a surface to be inspected, with a beam having non-uniform sectional intensity distribution, a uniforming system for substantially uniforming the sectional intensity distribution of the beam, and an inspecting portion for detecting scattered light from the surface to determine the state of the surface.

15 Claims, 11 Drawing Sheets

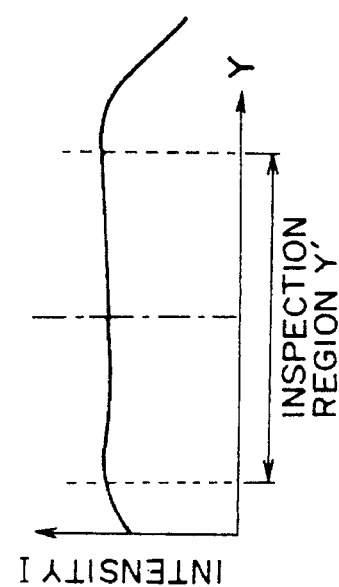
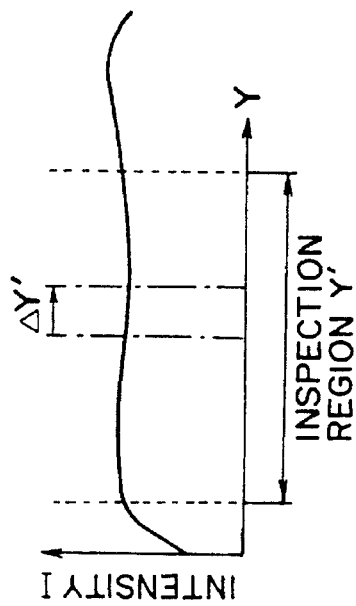
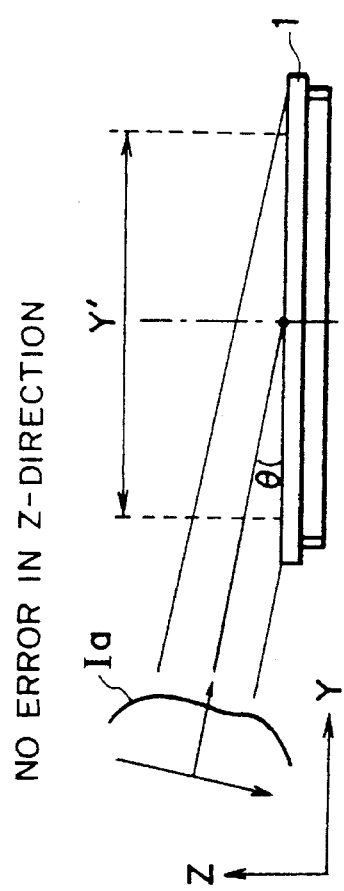
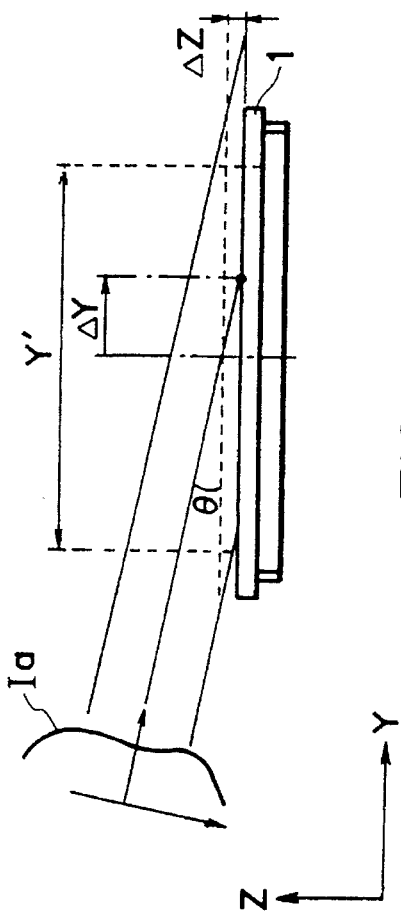

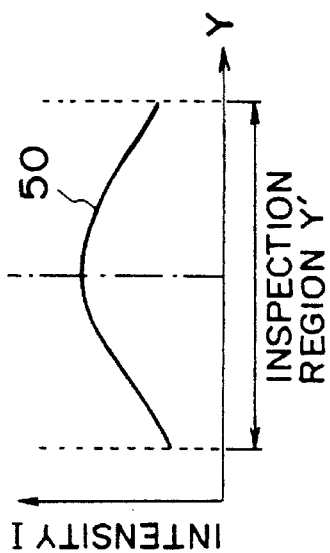
FIG. 5A(2)
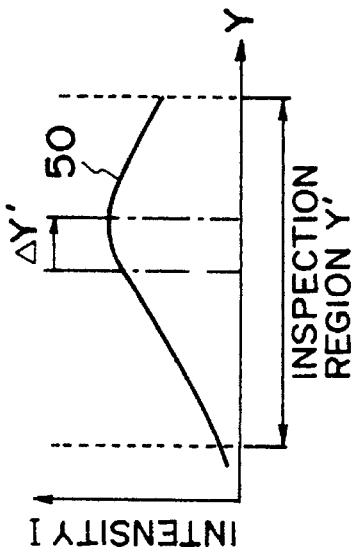
FIG. 5B(2)
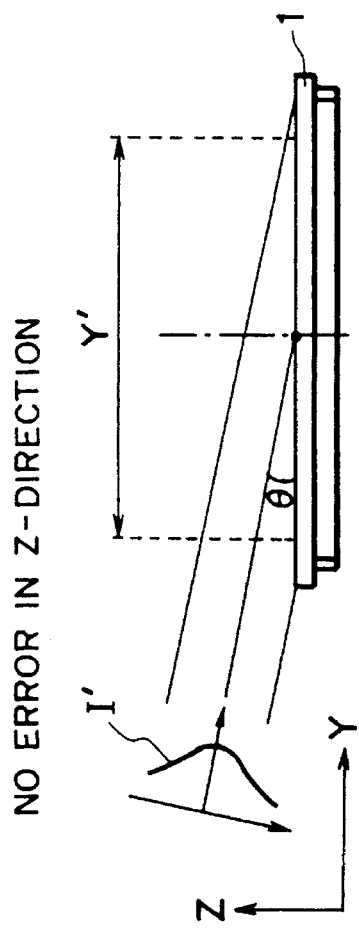
FIG. 5A(1)
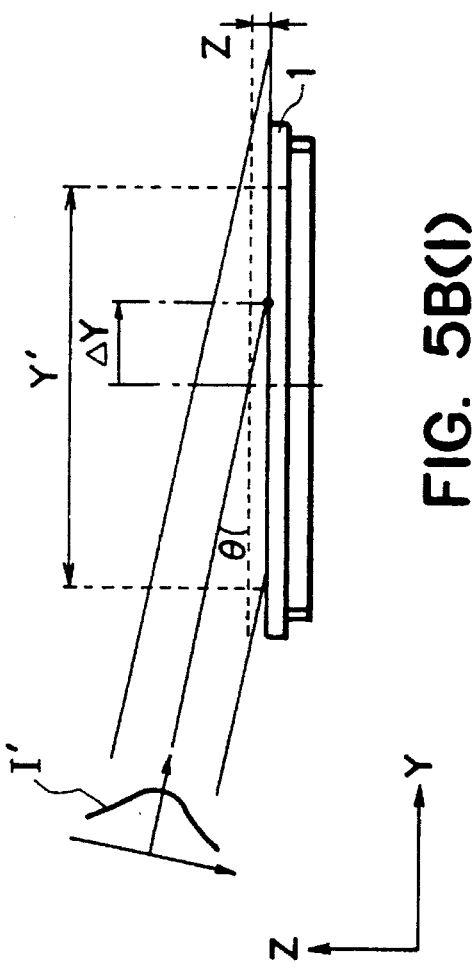
FIG. 5B(1)

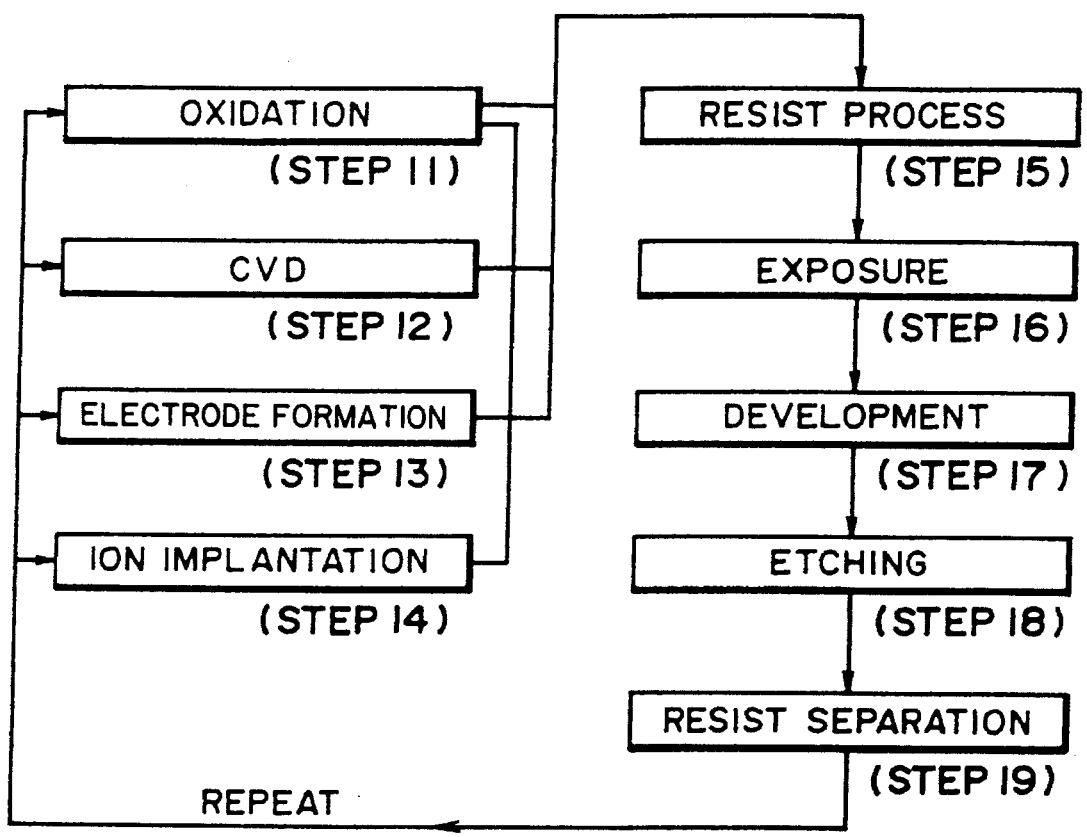
F I G. 12

SURFACE INSPECTING DEVICE USING BISECTED MULTI-MODE LASER BEAM AND SYSTEM HAVING THE SAME

This application is a continuation of application Ser. No. 08/281,607 filed Jul. 28, 1994, now abandoned.

FIELD OF THE INVENTION AND RELATED ART

This invention relates to a surface state inspecting device. More particularly, the invention is concerned with a surface state inspecting device for detecting, with good precision, presence/absence or the position of a foreign particle, if any, adhered to the surface of substrate, such as a reticle or photomask having a circuit pattern for manufacture of semiconductor devices such as ICs, LSIs, etc. or microdevices such as CCDs, liquid crystal panels or magnetic heads, for example, or adhered to the surface of a pellicle film mounted to such substrate for prevention of adhesion of a particle to the substrate. In another aspect, the invention is concerned with an exposure apparatus having such inspection device.

Generally, in IC or LSI manufacturing processes, a circuit pattern formed on a substrate such as a reticle or photomask is transferred to a resist coated wafer by means of an exposure apparatus (stepper or mask aligner).

In this pattern transfer process, if there is a pattern defect or a foreign particle such as dust on the substrate surface, also it is transferred to the wafer, thus decreasing yield of ICs or LSIs.

Particularly, when a reticle is used and a circuit pattern is repeatedly printed on many shot areas on a wafer through a step-and-repeat process, the presence of only one particle on the reticle may result in a large decrease of yield of ICs or LSIs since it is transferred to every area on the wafer surface.

To avoid this, in the IS or LSI manufacturing processes, it is necessary to detect presence/absence of a particle on a substrate. Generally, an inspection method based on isotropic light scattering property of a particle is used.

For example, parallel light is projected diagonally from the above onto the surface to be inspected, and scattered light from a particle is collected by an index distribution type microlens array to a one-dimensional image sensor (sensor array). The inspection is made on the basis of the thus imaged particle.

In a case where a laser beam from a semiconductor laser is projected obliquely on the surface to be inspected, as shown in FIG. 5A(1), since the laser beam has a sectional intensity distribution of Gaussian shape, as illustrated in FIG. 5A(2) a light intensity distribution 50 of Gaussian shape is formed in a linear inspection zone defined on the surface being inspected.

Here, if the surface being inspected has a set error $\Delta Z$ in the Z direction, as shown in FIG. 5B(1), the light intensity distribution 50 of the linear inspection zone defined on the surface shifts in the Y direction, as shown in FIG. 5B(2).

This leads to variation of detection sensitivity to a particle in the inspection zone.

SUMMARY OF THE INVENTION

It is accordingly an object of the present invention to provide a surface inspecting device by which a constant detection sensitivity in the detection zone is assured.

It is another object of the present invention to provide an exposure apparatus having such an inspection device.

In accordance with an aspect of the present invention, to achieve at least one of the above objects, there is provided a surface state inspecting device wherein a surface to be inspected is irradiated with a beam having non-uniform sectional intensity distribution, wherein scattered light caused by the surface is detected, and wherein the device includes means for making the sectional intensity distribution of the beam substantially uniform.

A surface inspecting device of the present invention may be used singly or it may be incorporated into an exposure apparatus for manufacture of semiconductor devices such as ICs or LSIs, or microdevices such as CCDs, liquid crystal panels, magnetic heads, for example.

Where a surface inspecting device of the present invention is used for inspection of presence/absence of a particle on a substrate, for manufacture of microdevices, or on a pellicle for protection of such reticle against a particle, the possibility of failure of detection of such particle is reduced and, therefore, the yield of microdevices is increased.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIGS. 4A(1) and 4A(2), and 4B(1) and 4B(2) are graphs, respectively, for explaining advantageous results of the FIG. 1A arrangement.

FIGS. 5A(1) and 5A(2), and 5B(1) and 5B(2) are graphs, respectively, for explaining an effect of positional change of the surface, being inspected, in the Z direction, relative to the intensity distribution in the inspection zone.

FIGS. 6A and 6B are graphs, wherein FIG. 6A shows light intensity distribution on the surface being inspected, where a single-mode emission laser is used, and wherein FIG. 6B shows wavelength spectrum distribution of such laser.

FIGS. 7A and 7B are graphs, wherein FIG. 7A shows light intensity distribution on the surface being inspected, where a multi-mode emission laser is used, and wherein FIG. 7B shows wavelength spectrum distribution of such laser.

FIGS. 8A and 8B are graphs, wherein FIG. 8A shows wavelength spectrum distribution of a multi-mode emission laser, and wherein FIG. 8B shows coherent length distribution of such laser.

FIG. 12 is a flow chart of a wafer process of FIG. 11.

DESCRIPTION OF THE PREFERRED EMBODIMENTS

Figure 1A:
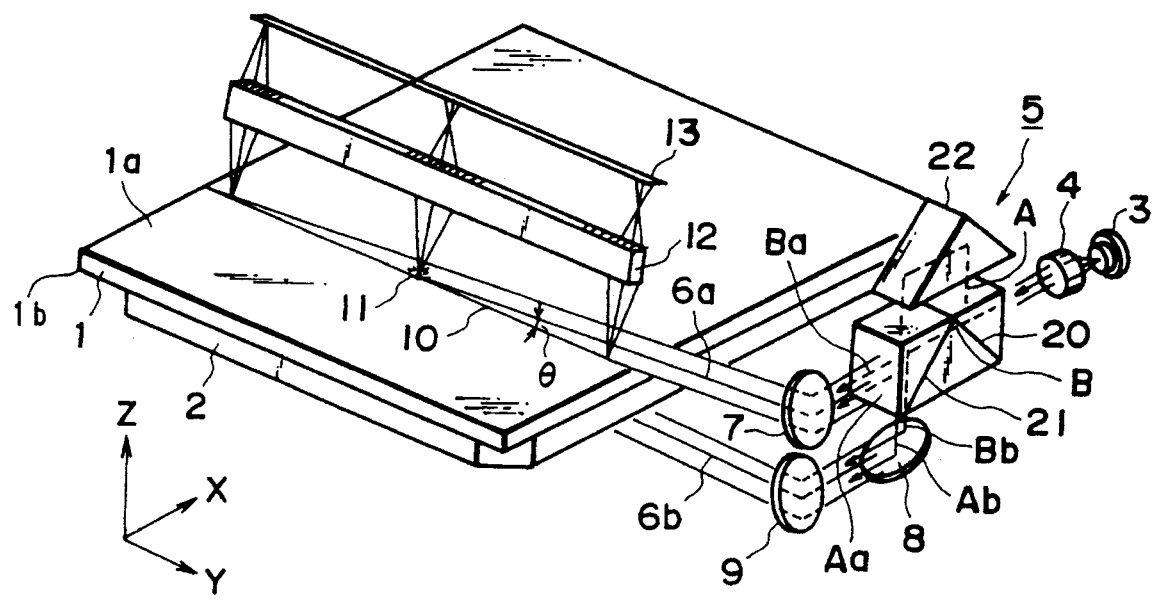
FIGS. 1A and 1B are perspective views, respectively, schematically showing an inspecting device according to an embodiment of the present invention.
Figure 1B:
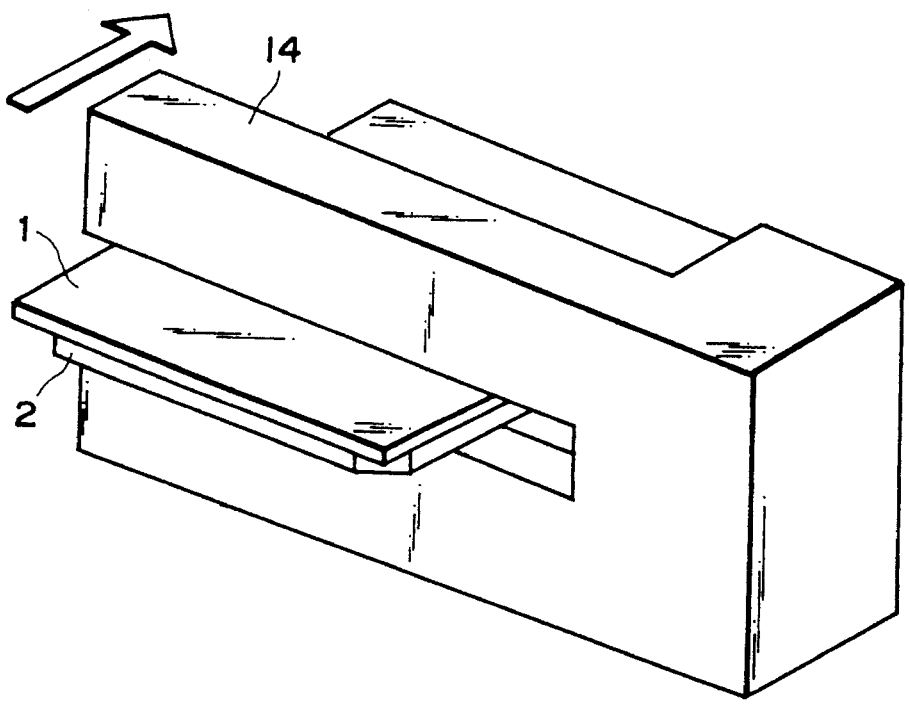

FIGS. 1A and 1B show an embodiment of the present invention, wherein FIG. 1A shows the an optical arrangement and wherein FIG. 1B shows outside appearance.

Laser light emitted by a multi-mode semiconductor laser 3 has a certain divergent angle, and it is transformed by a collimator lens 4 into a parallel light. This light is then received by an intensity distribution uniforming device (20–22) which is an important feature of the present invention.

Laser light (parallel light) is divided by a beam splitter 20 into two light beams of the same intensity. Transmitted light B enters a beam splitter 21, while reflected light A is reflected twice by a corner cube 22 and it enters the beam splitter 21. Here, since the corner cube 22 has been set with a shift of a predetermined amount L/2 in the X direction, lights Aa and Ba emitted from the beam splitter 21 in the X direction after the lights A and B are combined with each other by the beam splitter 21, are parallel lights, parallel to each other. The lights Aa and Ba have an interval L between their centers.

The beam splitter 21 comprises a half mirror and, for this reason, lights Ab and Bb are emitted therefrom in the Z direction. The lights Ab and Bb have an interval L between their centers. Thus, combined lights Aa+Ba and Ab+Bb emitted in two directions as lights 6a and 6b. They are the lights for inspection of a blank surface 1a of a reticle and for inspection of a lower pellicle surface, respectively.

The blank surface inspecting light 6a has a substantially uniform sectional intensity distribution, and it is projected by a mirror 7 obliquely on the blank surface 1a at a predetermined angle θ. The lower pellicle surface inspecting light 6b has a substantially uniform sectional intensity distribution, and it is projected by mirrors 8 and 9 obliquely on the lower pellicle surface 1b at a predetermined angle θ. As a result, a linear illumination zone 10 extending in the Y direction is defined on each surface, to be inspected, by the corresponding laser beam. In each linear illumination zone, non-uniformness of intensity is small.

For simplicity of explanation, the embodiment will be explained only with reference to the inspection of the blank surface 1a which is the bottom surface of the reticle 1.

If a particle 11 is present on the illumination zone 10, scattered light is produced by the particle 11. The scattered light is imaged on a line sensor 13 by a scattered light receiving imaging lens 12, disposed along the illumination zone 10. In this embodiment, the scattered light receiving lens comprises an array lens such as an index distribution type lens array. However, it may comprise an imaging lens such as of an ordinary camera lens or a Fourier transformation lens.

As shown in FIG. 1B, the optical system assembly 14 is relatively moved in the X direction which intersects (perpendicularly) with the illumination zone 10, by which the whole surface of the reticle is inspected.

Details of intensity distribution uniforming device 5 will be explained with reference to FIGS. 2–4.

Figure 2:
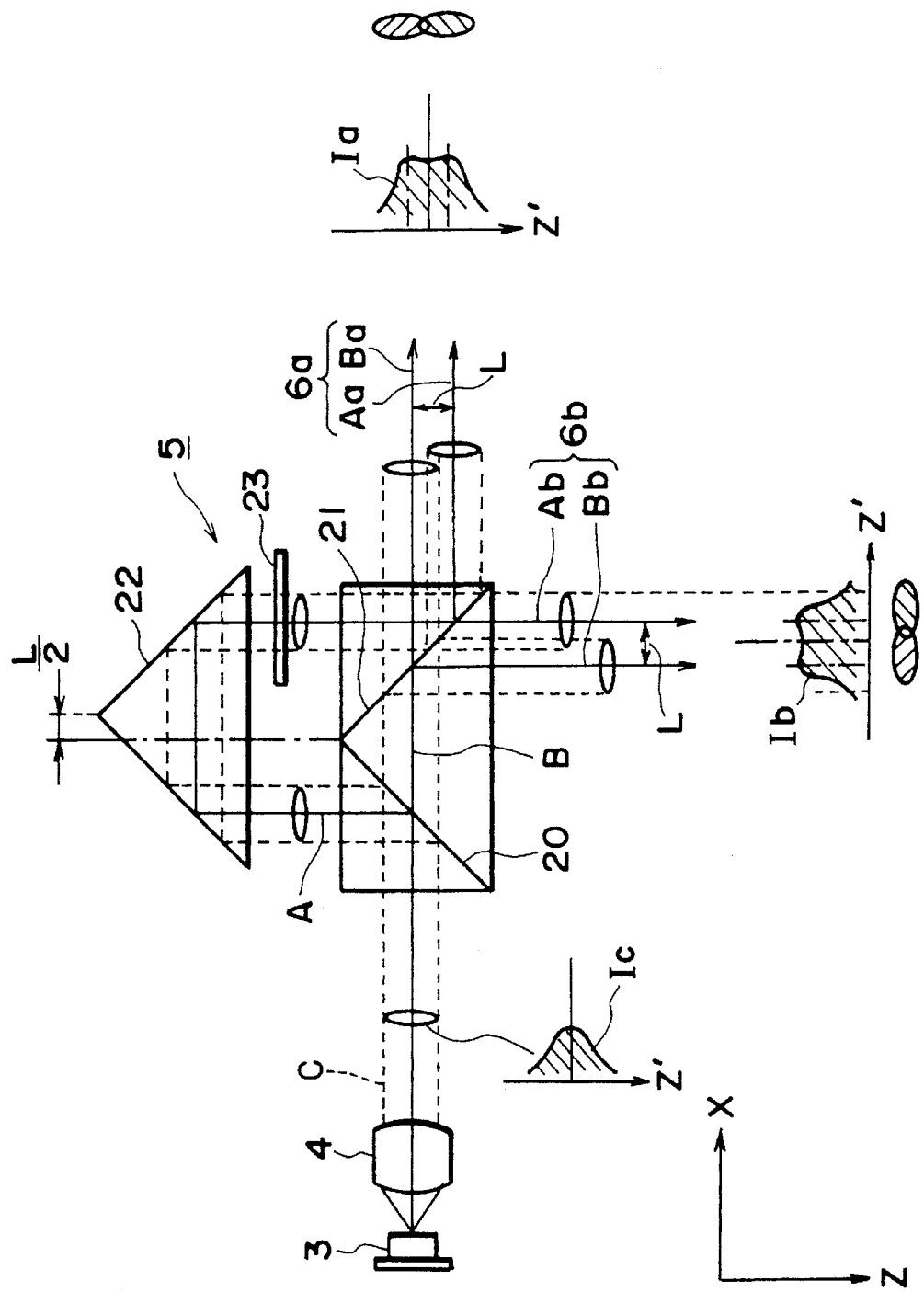
FIG. 2 is a sectional view of intensity distribution uniforming means of the FIG. 1A embodiment.

FIG. 2 is a sectional view of the intensity distribution uniforming device 2. In FIG. 2, parallel light flux C emitted from the collimator lens 4 has a sectional intensity distribution Ic of Gaussian shape.

The parallel light flux C is divided by the beam splitter 20 into two lights A and B of the same intensity. Transmitted light B goes straight directly to the beam splitter 21. Reflected light A is reflected twice by the corner cube 22, whereby the light path is folded and the light is directed to the beam splitter 21. These two lights A and B are recombined by the beam splitter 21. Since however the corner cube 22 is set with a shift of predetermined amount L/2 in the X direction, lights Aa and Ba and lights Ab and Bb, emerging from the beam splitter 21 after the lights A and B are combined, are parallel lights, parallel to each other, having an interval L between their centers.

Figure 3:
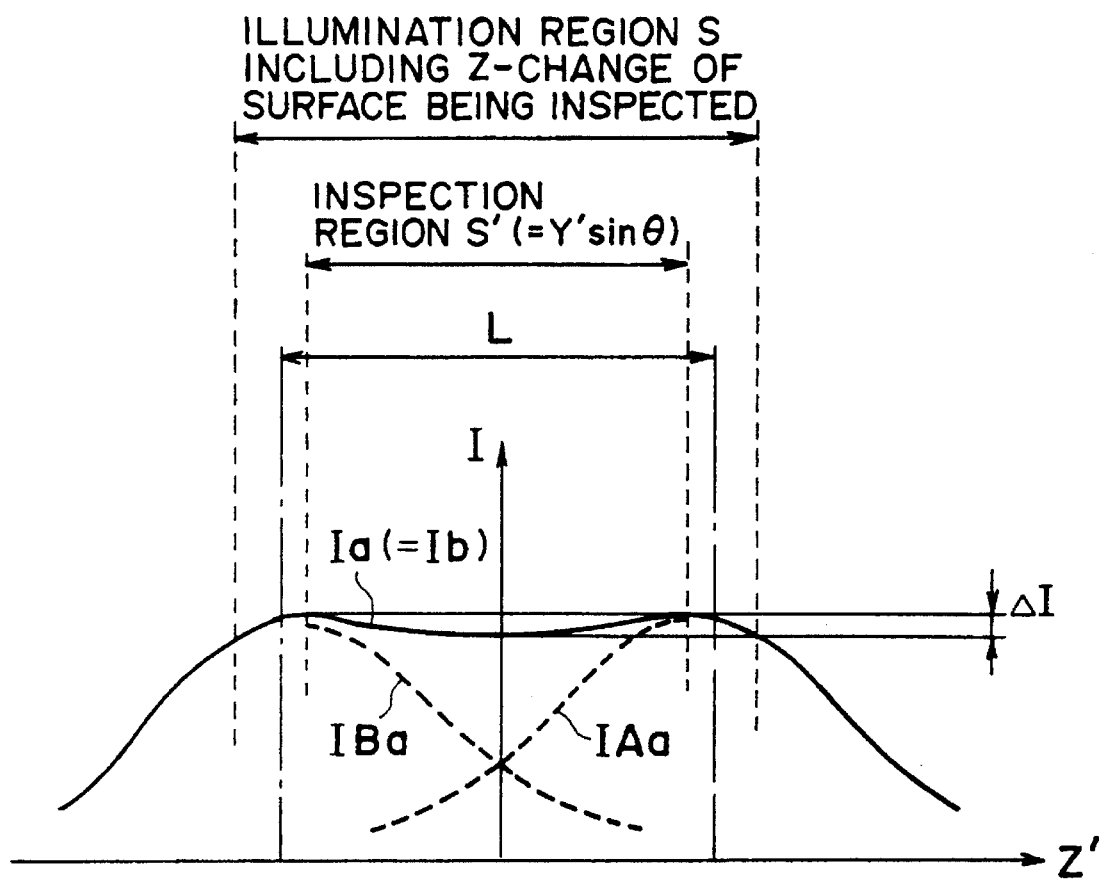
FIG. 3 is a graph view for explaining sectional intensity distribution of a beam produced by the intensity distribution uniforming means of FIG. 1A.

FIG. 3 is a sectional view for explaining the light resulting from combining the lights Aa and Ba.

With a parallel shift L of the interval between centers of the two lights Aa and Ba, the Gaussian distributions of them are relatively deviated and overlapped to provide a substantially uniform intensity distribution (FIG. 3) within a range of the diameter S of light necessary for the inspection, this being able to meet a set error ΔZ of the surface 1a to be inspected, in the Z direction. Here, the light beam diameter S necessary for the inspection is related to the inspection zone Y' on the reticle 1 and the set error ΔZ of the reticle 1 in the Z direction as well as the incidence angle θ of the inspecting light 6a for the reticle 1, and it is given by the following equation:

$$S=(Y'+\Delta Z/\tan\theta)\sin\theta \tag{1}$$

Further, the intensity distributions Ia and Ib (Ib denotes the intensity distribution of the light 6b) resulting from the overlap of beams shown in FIG. 3, are related to the amount L of shift of the light and the intensity distribution Ic (the light beam diameter at the center intensity $1/e^2$ value is w) of the parallel light from the collimator lens 4, and they can be calculated in accordance with the following equations (Z' is the coordinate axis in the radial direction of light):

$$Ic=\exp\{-8(Z'/w)^2\} \tag{2}$$

$$Ia=Ib=\{\exp[-8((Z'+L/2)/w)^2]+\exp[-8((Z'-L/2)/w)^2]\}/2 \tag{3}$$

By optimizing L and w in equation (3), it is possible to reduce non-uniformness ΔI of intensity to ±1.5% or less, within the light beam diameter S necessary for the inspection, this being able to meet a positional change of the reticle in the Z direction.

In the arrangement of this embodiment, the interval L between the centers of two lights can be set as desired by moving the corner cube 22 in the X direction (FIG. 2). Thus, adjustment can be made to obtain uniform sectional intensity distribution independently of the diameter of light entering the corner cube 22.

If the incident light C comprises linearly polarized light, the reflecting surface of the beam splitter 20 and the half mirror surface of the beam splitter 21 may be provided with multilayered films having transmissivity and reflectivity, respectively, set with respect to the direction of polarization of the incident light C. In that occasion, the linear polarization state of the light having its intensity distribution uniformed can be maintained in the same state as of the incident light C.

The foregoing description has been made on an assumption that the division ratio of each of the beam splitters 20 and 21 is exactly 1:1. Actually, however, the division ratio may not exactly be 1:1 because of an error in manufacture or for any other reason. In that occasion, a light quantity adjusting member 23 such as an ND filter may be inserted into the light path of the beam A to allow adjustment to remove a difference in intensity of the two beams, and the beam profile of combined light may be controlled.

Since laser has high coherency, an adverse effect due to interference of laser beams may occur. However, in this embodiment, by setting the optical path difference between the lights A and B (FIG. 2) so that it becomes longer than the coherence length of the laser 3, it is possible to avoid an adverse effect of interference of two beams.

In accordance with this embodiment, as described, a desired sectional intensity distribution can be provided. It is possible to form a uniform intensity distribution such as shown in FIG. 4A on the surface to be inspected. Thus, by uniforming the intensity distribution in the necessary illumination zone, being able to meet the error of the surface in the Z direction, it is assured to obtain uniform signal level regardless of a shift of intensity distribution of illumination light attributable to Z change of the surface to be inspected. Thus, it is not necessary to control and hold the Z position of the surface to be inspected.

Figure 6A:
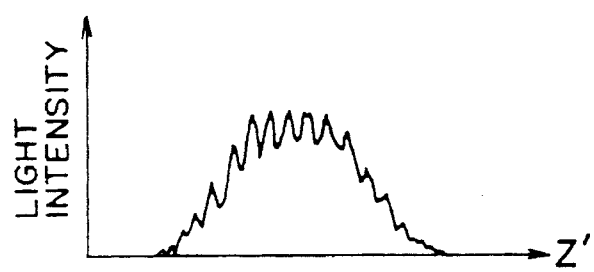
Figure 6B:
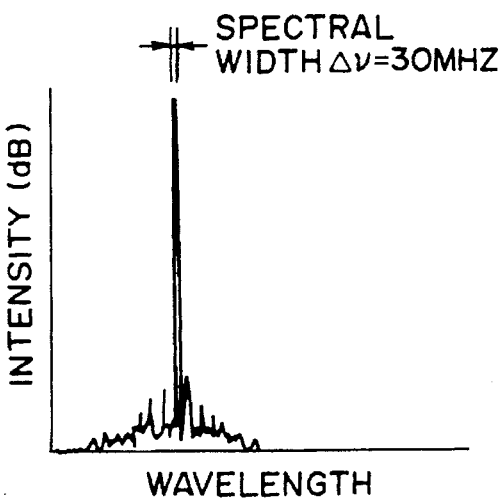

Now, description will be made on light intensity distribution on the surface $1a$, to be inspected, in an occasion where a single-mode (emission longitudinal mode) laser is used in place of the semiconductor laser 3 and where two lights A and B are superposed one upon another without making the optical path difference of the two lights A and B larger than the coherence length. FIG. 6A shows light intensity distribution in the case where the interference between the lights A and B is strongest. Due to the interference, the light intensity distribution on the surface $1a$, being inspected, is not uniform. FIG. 6B shows an example of spectrum distribution of a single-mode emission laser. Since the spectral width $\Delta v$ is narrow (30 MHz), the coherence length is about 5 m. Thus, to avoid interference of lights A and B, an optical path difference longer than this is necessary.

Figure 7A:
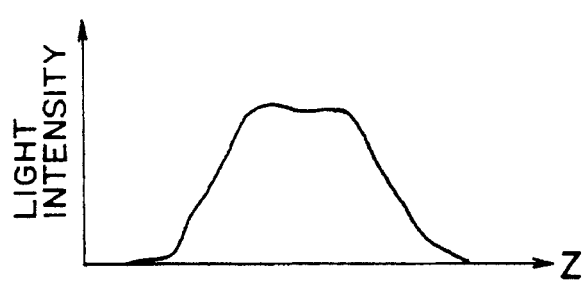

FIG. 7 shows an example of light intensity distribution upon the surface $1a$ where the semiconductor laser 3 is replaced by a laser of spectral width 4 nm and where the two lights are superposed upon one another. No interference occurs between the lights A and B, and the light intensity distribution upon the surface $1a$ is uniform. Since this laser has a wide spectral width $\Delta v$ (4 nm), the coherence length is 0.1 mm. The optical path difference between the lights A and B in the FIG. 1 arrangement is larger than this, and no interference occurs between them.

Figure 7B:
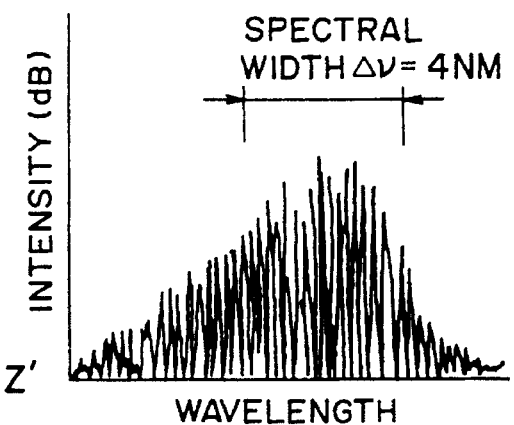
Figure 8A:
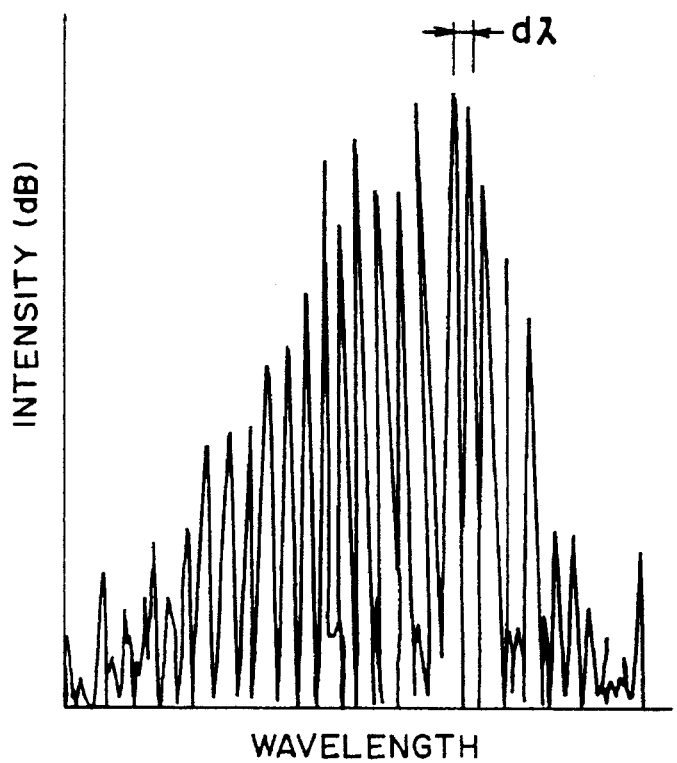
Figure 8B:
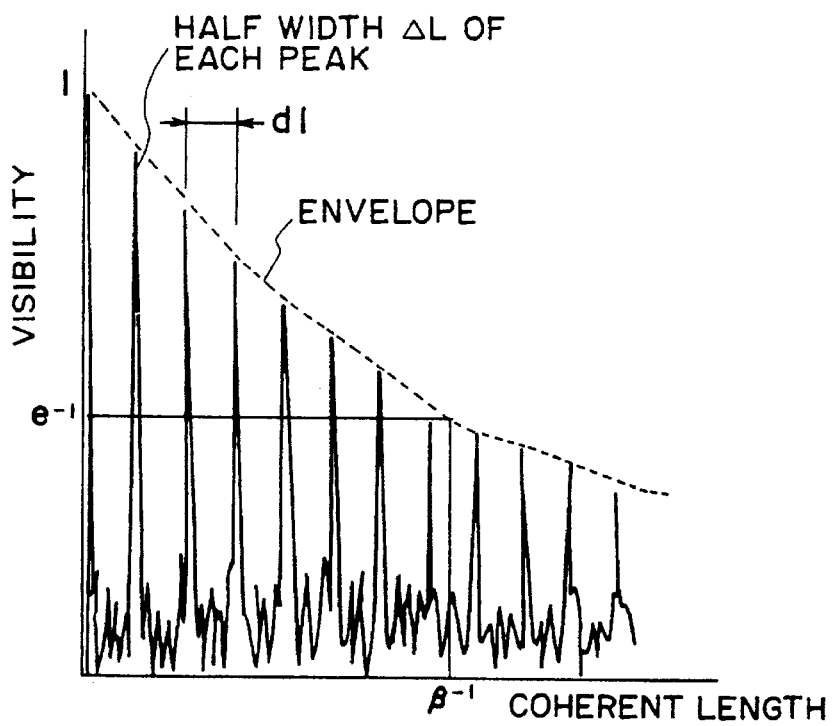

FIG. 7B shows an example of spectrum distribution of a multi-mode emission laser. As illustrated, the spectral width is 4 nm which is wider than that of the single-mode emission laser. However, because of combination of modes of narrow spectral widths, there is a case where interference occurs between two lights even if the optical path difference is made longer than the coherence length. In this case, it is not possible to uniform the light intensity distribution. This is because: due to combination of modes of narrow spectral widths as described, the actual coherence length has discrete peaks at regular intervals such as shown in FIG. 8B. When the optical path difference just corresponds to the discrete peak position of the visibility interference intensity, the two light interfere with each other.

Thus, in this embodiment, the optical path difference of the lights A and B is shifted from the peak position of visibility, by an amount not less than a half width of the mode having that peak, to thereby avoid interference of the lights A and B.

This will now be explained in more detail. FIG. 8 shows an example of spectrum distribution of a multi-mode semiconductor laser. As described, the spectrum distribution of a multi-mode semiconductor laser comprises combination of modes of narrow spectral widths, and each mode is produced with a certain distance $d\lambda$ determined by a resonator of the laser. FIG. 8B shows coherence length of the multi-mode laser of FIG. 8A. It has discrete peaks at regular intervals $d1$ which is given by:

$$d1 \approx \lambda^2/d\lambda \text{(mm)} \quad (4)$$

It is a value as determined by the resonator of the laser. If such discrete visibility peak position and the optical path difference coincide with each other, the two beams interfere with each other, such that it is not possible to obtain uniform light intensity distribution on the surface to be inspected.

Thus, to avoid this, the optical path difference d between the two lights may be set as follows:

$$n \times d1 + \Delta L/2 < d < (n+1) \times d1 - \Delta L/2 \quad (5)$$

where n is an integer and $\Delta L$ is a half width of one peak. When this is done, there occurs no interference between the two lights and, thus, uniform light intensity distribution is obtainable.

Even where d satisfies relation (5), if n is small, there is a case where small interference occurs between the two lights. In that occasion, an envelop such as shown in FIG. 8B is considered. This envelop is determined by one spectral width of multi-mode emission spectrums of FIG. 8A, and if the coherence length in this envelop is denoted by $\Delta l'$, then:

$$m \times d1 + \Delta L/2 < d < (m+1) \times d1 - \Delta L/2 \quad (6)$$

where m is an integer which satisfies $\Delta l' < m \cdot d1$ By selecting d satisfying this relation, it is possible to obtain a light intensity distribution without interference.

If the spectrum of laser is of Lorentz type, $\Delta l'$ can be given by:

$$\Delta l' = \pi \beta^{-1} \quad (7)$$

where $\beta$ is an inverse of $\Delta l$ as the visibility v becomes equal to $e^{-1}$.

While a multi-mode emission semiconductor laser is used in this embodiment as a light source, a single-mode emission semiconductor laser may be used. If this is used, high frequency modulation may be done to the semiconductor laser (high frequency superposition) to expand the spectral width. By such high frequency superposition, the spectrum of a single-mode emission semiconductor laser of FIG. 6B is replaced by a spectrum distribution of multi-mode emission laser (FIG. 7B). By setting the optical path difference between the two lights A and B in accordance with equation (6), it is possible to avoid interference between the lights A and B such that a uniform light intensity distribution is provided on the surface $1a$.

Figure 9:
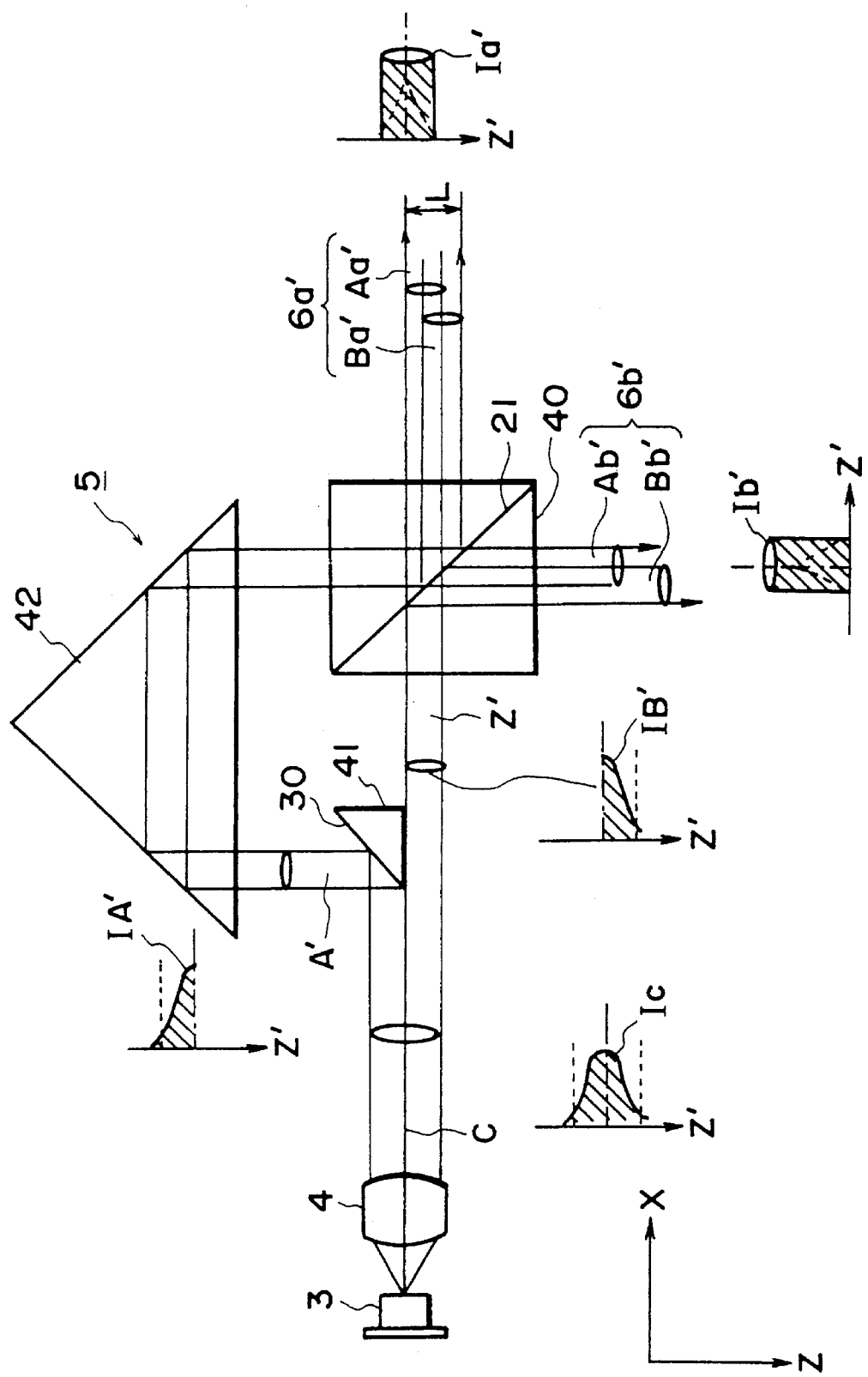
FIG. 9 is a schematic view of another embodiment of the present invention.

FIG. 9 shows another embodiment of the present invention. The first light dividing member used in the preceding embodiment serves to amplitude-divide the incident light. In this embodiment, on the other hand, a total reflection mirror surface 30 is used as the first light dividing member to bisect the incident light from the center of the beam (wavefront division). Substantially the same result is attainable. The remaining portion of this embodiment is similar to the preceding embodiment.

Particularly, since in this embodiment the first light dividing member comprises wavefront dividing means, the center intensity of the light B is held at the initial level. In the preceding embodiment, since the first light dividing means comprises amplitude dividing means, the center intensity of the light B becomes ½ of its initial level. In both of these embodiments, the means for combining the lights A and B comprises amplitude dividing means, finally the beam center intensity after the intensity distribution is uniformed is in this embodiment twice as large as that of the preceding embodiment.

A particle inspecting device such as described hereinbefore may be used singly or it may be incorporated into an exposure apparatus for manufacture of semiconductor devices such as ICs or LSIs or microdevices such as CCDs, liquid crystal panels, magnetic heads, etc.

It is to be noted that the sectional intensity distribution uniforming means may take a form other than that described above.

Figure 10:
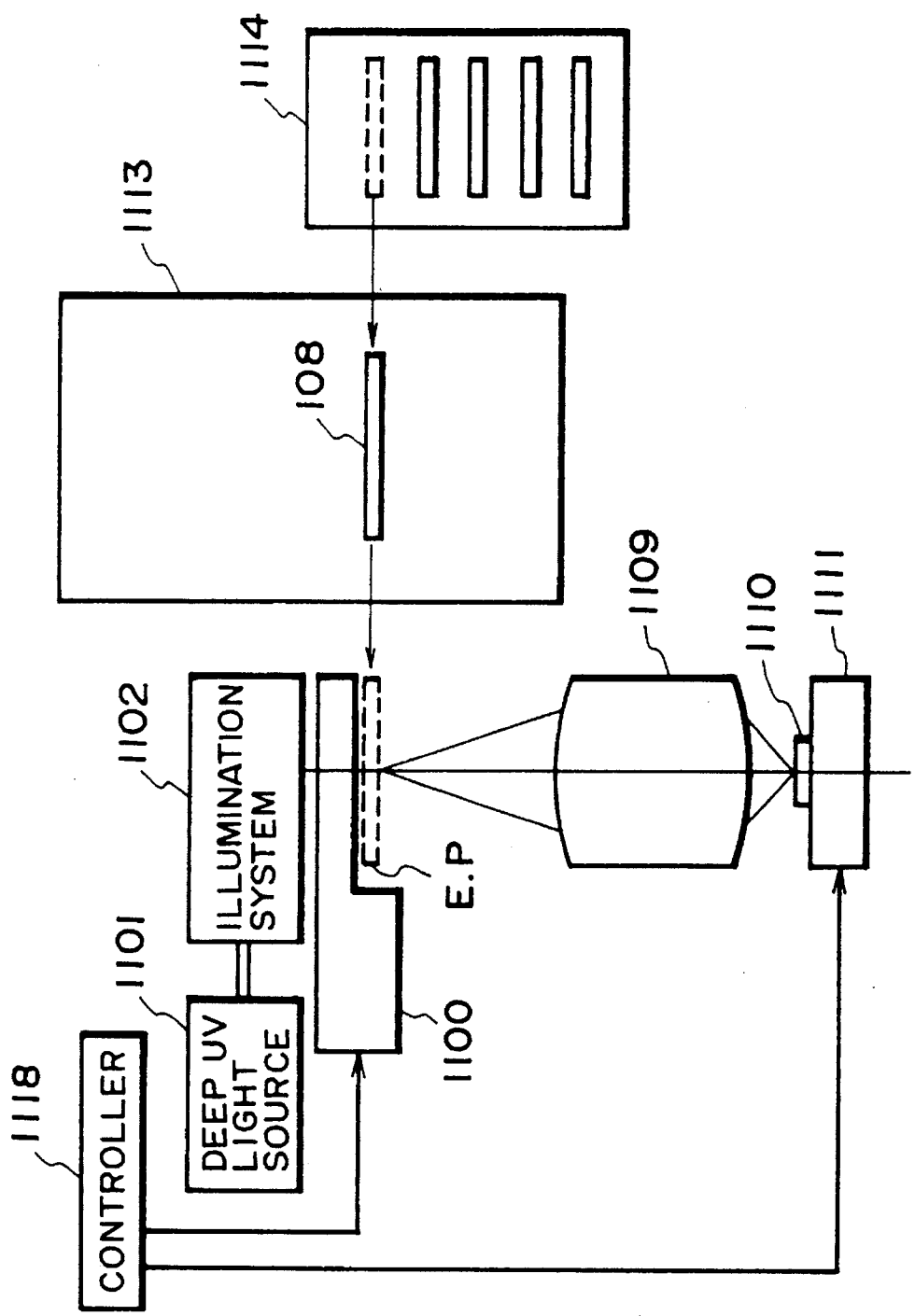
FIG. 10 is a schematic view of an exposure apparatus according to an embodiment of the present invention.

FIG. 10 is a schematic view of a surface state inspecting device according to a further embodiment of the present invention. In this embodiment, the inspecting device as a whole is incorporated into a semiconductor printing apparatus.

Denoted at 1101 is a deep ultraviolet light source such as an excimer laser. Denoted at 1102 is an illumination system unit which serves to illuminate, at once, the whole region to be inspected of a reticle 108 uniformly from the above, with a predetermined numerical aperture (NA).

Denoted at 1109 is a ultra high resolution lens system (or mirror system) for transferring a reticle pattern onto a wafer 1110. During printing operation, exposures are made while moving the shots one by one in accordance with the step feeding of the wafer moving stage 111. Denoted at 1110 is an alignment optical system for aligning the reticle and the wafer prior to the exposure operation. It includes at least one reticle observing microscope system.

Denoted at 1114 is a reticle changer unit in which plural reticles can be accommodated (stand-by). Denoted at 1113 is a particle inspecting unit which is arranged in accordance with the features of the preceding embodiment. This unit serves to execute particle inspection to a reticle before it is taken out from the reticle changer and is placed at the exposure station (E and P in the drawing).

Controller 1118 serves to control sequential operations such as alignment operation, exposure operation and wafer step feeding operation which are basic operations of a stepper.

Now, an embodiment of a device manufacturing method which uses an exposure apparatus such as described above will be explained.

Figure 11:
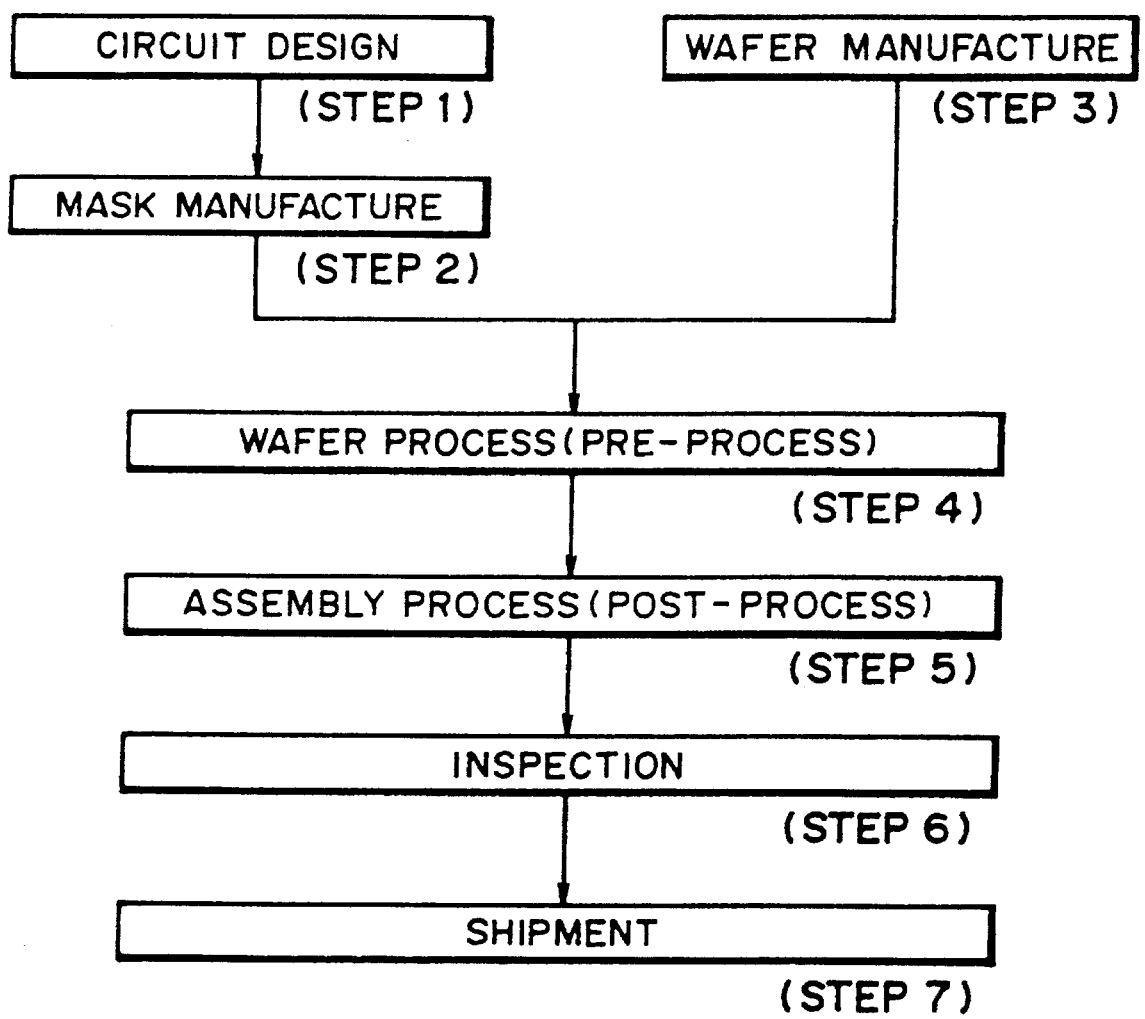
FIG. 11 is a flow chart of semiconductor device manufacturing processes.

FIG. 11 is a flow chart of the sequence of manufacturing a semiconductor device such as a semiconductor chip (e.g. IC or LSI), a liquid crystal panel or a CCD, for example. Step 1 is a design process for designing the circuit of a semiconductor device. Step 2 is a process for manufacturing a mask on the basis of the circuit pattern design. Step 3 is a process for manufacturing a wafer by using a material such as silicon.

Step 4 is a wafer process which is called a pre-process wherein, by using the so prepared mask and wafer, circuits are practically formed on the wafer through lithography. Step 5 subsequent to this is an assembling step which is called a post-process wherein the wafer processed by step 4 is formed into semiconductor chips. This step includes assembling (dicing and bonding) and packaging (chip sealing). Step 6 is an inspection step wherein operability check, durability check and so on of the semiconductor devices produced by step 5 are carried out. With these precesses, semiconductor devices are finished and they are shipped (step 7).

FIG. 12 is a flow chart showing details of the wafer process. Step 11 is an oxidation process for oxidizing the surface of a wafer. Step 12 is a CVD process for forming an insulating film on the wafer surface. Step 13 is an electrode forming process for forming electrodes on the wafer by vapor deposition. Step 14 is an ion implanting process for implanting ions to the wafer. Step 15 is a resist process for applying a resist (photosensitive material) to the wafer. Step 16 is an exposure process for printing, by exposure, the circuit pattern of the mask on the wafer through the exposure apparatus described above, the mask having been inspected by the particle inspecting device as described hereinbefore.

Step 17 is a developing process for developing the exposed wafer. Step 18 is an etching process for removing portions other than the developed resist image. Step 19 is a resist separation process for separating the resist material remaining on the wafer after being subjected to the etching process. By repeating these processes, circuit patterns are superposedly formed on the wafer.

While the invention has been described with reference to the structures disclosed herein, it is not confined to the details set forth and this application is intended to cover such modifications or changes as may come within the purpose of the improvements or the scope of the following claims.

What is claimed is:

1. A surface state inspecting device, comprising:

illumination means having a beam source, for illuminating a surface to be inspected, wherein said beam source includes a multi-mode laser with respect to emission longitudinal mode;

uniforming means for substantially uniforming the sectional intensity distribution region of said surface, wherein said uniforming means includes means for bisecting said beam and means for re-combining two divided beams so that a distribution resulting from combined sectional intensity distributions of the two beams become substantially uniform; and inspecting means for detecting scattered light from the surface to determine the state of the surface.

2. A device according to claim 1, wherein said beam comprises a parallel beam.

3. A device according to claim 1, wherein said illumination means projects the beam obliquely on the surface so that a substantially linear illumination zone is defined on the surface.

4. A device according to claim 3, wherein the beam is incident on the surface at a set incidence angle of 0.5–6.5 (deg.).

5. A device according to claim 1, wherein said illumination means comprises a semiconductor laser and a collimator lens for producing the beam.

6. A device according to claim 5, wherein said semiconductor laser comprises a multi-mode laser with respect to emission longitudinal mode.

7. A device according to claim 5, wherein said semiconductor laser comprises a single-mode laser which is high-frequency modulated to provide multi-mode emission.

8. A device according to claim 1, wherein said uniforming means provides two lights of uniform sectional intensity distributions, each of which is directed to a corresponding surface to be inspected.

9. A device according to claim 1, further comprising means for relatively moving said beam relative to the surface.

10. A surface state inspecting device, comprising:

illumination means having a beam source, for illuminating a surface to be inspected, wherein said beam source provides a beam having non-uniform sectional intensity distribution;

uniforming means for substantially uniforming the sectional intensity distribution of said beam at least within an inspection region of said surface; and inspecting means for detecting scattered light from the surface to determine the state of the surface wherein said uniforming means includes means for bisecting said beam and means for re-combining divided two beams so that a distribution resulting from combined sectional intensity distributions of the two beams becomes substantially uniform; and wherein the two beams have an optical path difference which does not coincide with the positions of discrete interference peaks produced and dependent upon the optical path difference.

11. A device according to claim 10, wherein the optical path difference of the two beams is positioned away from the position of the interference peak by at least a half width of that peak.

12. A device according to claim 11, wherein the optical path difference of the two beams is at least as great as a coherence length of a laser from which the two beams are emitted.

13. An exposure system, comprising:

an exposure apparatus for performing an exposure to a substrate; and an inspecting device for inspecting a state of a surface to be inspected;

wherein said inspecting device has an illumination means having a beam source for illuminating a surface to be inspected, wherein said beam source includes a multi-mode laser with respect to emission longitudinal mode; uniforming means for substantially uniforming the sectional intensity distribution region of said surface, wherein said uniforming means includes means for bisecting said beam and means for re-combining divided two beams so that a distribution resulting from combined sectional intensity distributions of the two beams become substantially uniform, and inspecting means for detecting scattered light from the surface to determine the state of the surface.

14. A method wherein a laser beam from a multi-mode laser with respect to emission longitudinal mode is divided into two beams and wherein the two beams are made incoherent with respect to each other, said method comprising:

setting an optical path difference of the two beams so that it does not coincide with discrete interference peak positions produced and dependent upon the optical path difference.

15. An optical illumination system, comprising:

illumination means having a beam source, for illuminating a surface to be inspected, wherein said beam source includes a multi-mode laser with respect to emission longitudinal mode; and uniforming means for substantially uniforming the sectional intensity distribution region of said surface, wherein said uniforming means includes means for bisecting said beam and means for re-combining divided two beams so that a distribution resulting from combined sectional intensity distributions of the two beams becomes substantially uniform.

* * * * *

UNITED STATES PATENT AND TRADEMARK OFFICE
CERTIFICATE OF CORRECTION

PATENT NO. 5,581,348      Page 1 of 2
DATED     December 3, 1996
INVENTOR(S) Miura, et al.

It is certified that error appears in the above-indentified patent and that said Letters Patent is hereby corrected as shown below:

On title page, item
[56] References Cited:

FOREIGN PATENT DOCUMENTS

"04152545     5/1992     Japan
04188746     7/1992     Japan" should read

--4-152545     5/1992     Japan
4-188746     7/1992     Japan--.

COLUMN 3:

Line 56, "device 2." should read --device 5.--.

UNITED STATES PATENT AND TRADEMARK OFFICE
CERTIFICATE OF CORRECTION

PATENT NO. 5,581,348

DATED : December 3, 1996

INVENTOR(S) : Miura, et al.

It is certified that error appears in the above-indentified patent and that said Letters Patent is hereby corrected as shown below:

COLUMN 5:

Line 48, "light" should read --lights--.

COLUMN 6:

Line 20, "$\Delta 1' < m \cdot d1$" should read --$\Delta 1' < m \cdot d1.$--.

Signed and Sealed this

Twentieth Day of May, 1997

Attest:

Attesting Officer

BRUCE LEHMAN

Commissioner of Patents and Trademarks